US010456595B2

United States Patent
Ribbing et al.

(10) Patent No.: US 10,456,595 B2
(45) Date of Patent: Oct. 29, 2019

(54) PORTAL IMAGING FOR BRACHYTHERAPY

(71) Applicant: KONINKLIJKE PHILIPS N.V., Eindhoven (NL)

(72) Inventors: Carolina Ribbing, Aachen (DE); Raymond Chan, San Diego, CA (US); Luis Felipe Gutierrez, Jersey City, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 508 days.

(21) Appl. No.: 14/904,121

(22) PCT Filed: Jul. 7, 2014

(86) PCT No.: PCT/IB2014/062905
§ 371 (c)(1),
(2) Date: Jan. 11, 2016

(87) PCT Pub. No.: WO2015/008188
PCT Pub. Date: Jan. 22, 2015

(65) Prior Publication Data
US 2016/0193480 A1  Jul. 7, 2016

Related U.S. Application Data

(60) Provisional application No. 61/847,284, filed on Jul. 17, 2013.

(51) Int. Cl.
*A61N 5/10* (2006.01)
*A61B 34/20* (2016.01)

(52) U.S. Cl.
CPC ......... *A61N 5/1039* (2013.01); *A61N 5/1001* (2013.01); *A61N 5/1049* (2013.01);
(Continued)

(58) Field of Classification Search
CPC .. A61N 5/1039; A61N 5/1071; A61N 5/1001; A61N 5/1064; A61N 5/1049;
(Continued)

(56) References Cited

U.S. PATENT DOCUMENTS 7,322,929 B2   1/2008  Lovoi
7,513,861 B2 * 4/2009  Klein ................... A61N 5/1015
                                                          600/3
(Continued)

FOREIGN PATENT DOCUMENTS

WO         01/82995       11/2001
WO       2005/005381       1/2005
(Continued)

OTHER PUBLICATIONS

Mao, "A fiducial detection algorithm for real-time image guided IMRT based on simultaneous MV and kV imaging", 2008.

*Primary Examiner* — Kaylee R Wilson

(57) ABSTRACT

A system for interventional brachytherapy for generating data to be used directly for therapy and/or for therapy planning includes a radiation source which irradiates tissue of a patient and one or more radiation detectors which detect radiation delivered to the patient and generate radiation dosage data indicative thereof. One or more position sensors determine the position of the radiation source and a localization unit, in communication with the one or more position sensors, generates position data indicative of the position of the radiation source. An image database stores one or more anatomical images of the patient. A dose calculation unit which co-registers the one or more anatomical images with the positional and radiation dosage data and generates dose monitoring data based on the co-registration.

15 Claims, 2 Drawing Sheets

(52) U.S. Cl.
CPC ......... *A61N 5/1064* (2013.01); *A61N 5/1071* (2013.01); *A61B 2034/2051* (2016.02); *A61B 2034/2061* (2016.02); *A61N 2005/1022* (2013.01); *A61N 2005/1058* (2013.01)

(58) Field of Classification Search
CPC .... A61N 2005/1022; A61N 2005/1058; A61B 2034/2061; A61B 2034/2051
See application file for complete search history.

(56) References Cited

U.S. PATENT DOCUMENTS

| | | | |
|---|---|---|---|
| 2002/0049375 A1* | 4/2002 | Strommer | A61B 5/0066 600/407 |
| 2003/0229282 A1 | 12/2003 | Burdette | |
| 2005/0175148 A1 | 8/2005 | Smither | |
| 2006/0013523 A1* | 1/2006 | Childlers | A61B 1/00165 385/12 |
| 2006/0136167 A1* | 6/2006 | Nye | A61B 5/02055 702/127 |
| 2009/0010390 A1* | 1/2009 | Saoudi | A61N 5/1048 378/97 |
| 2010/0119032 A1 | 5/2010 | Yan | |
| 2010/0280374 A1* | 11/2010 | Roberts | A61N 5/1001 600/439 |
| 2012/0140887 A1 | 6/2012 | Mundy | |
| 2013/0204072 A1 | 8/2013 | Verard | |

FOREIGN PATENT DOCUMENTS

| | | |
|---|---|---|
| WO | 2007/120532 | 10/2007 |
| WO | 2012/034157 | 3/2012 |
| WO | 2012/127455 | 9/2012 |

\* cited by examiner

PORTAL IMAGING FOR BRACHYTHERAPY

CROSS REFERENCE TO RELATED APPLICATIONS

This application is a national filing of PCT application Serial No. PCT/IB2014/062905, filed Jul. 7, 2014, published as WO 2015/008188 on Jan. 22, 2015, which claims the benefit of U.S. Provisional Application No. 61/847,284 filed Jul. 17, 2013, which is incorporated herein by reference.

The present application relates to the therapeutic arts. It finds particular application in conjunction with high dose rate (HDR) brachytherapy and will be described with particular reference thereto. However, it is to be appreciated that the invention will also find application in conjunction with other therapeutic treatments, such as low dose brachytherapy, positioning other treatment sources, and the like.

The more focal radiotherapy (RT) grows, the more important dose monitoring becomes in order to track and adapt dose to target volumes and critical structures. Portal imaging is the acquisition of images with a radiotherapy beam. Images from these devices are then used e.g. to verify a patient's treatment. In orthogonal ray imaging and in-beam PET, absorbed dose, patient positioning, organ motion/deformation is monitored in situ during external beam RT. During portal imaging, target volumes and organ motions are monitored, e.g. intrafraction breathing, interfraction tissue density modification, cavity filling, wall thickening, as well as tumor swelling and regression can be detected. In brachytherapy, where a miniature x-ray source is inserted in vivo, the need for monitoring is even higher, since this RT is more focal than external beam using MeV photons. Movement of critical structures or risk organs motivates dose monitoring.

In brachytherapy, the radiation source is not fixed but moveable. Various brachytherapy techniques have been developed in which a radiation source is placed inside the body. For example, low dose rate seeds can be permanently implanted in the target area. For accurate placement, the location of the tip of the catheter from which each seed is discharged needs to be known accurately. In high dose rate brachytherapy, a single high dose rate radioisotope is placed on the end of the catheter. The catheter is positioned adjacent the target and remains so positioned for a selected duration. The high dose rate seed may be repositioned to treat the target from various locations. The third option is to use a mini x-ray tube which is positioned at the tip of the catheter to irradiate the target.

When a moveable internal radiation source is used, portal imaging for monitoring dose delivery would be helpful. The exact position of the applicator as well as the exact position of the seed or any other radiation source is vital. Typically, an applicator is guided under real-time image guidance based on e.g. ultrasound (US) or x-ray, or it can be imaged after placement (based on e.g. computer tomographic CT techniques). Basing the placement on real-time ultrasonic imaging severely limits the placement accuracy due to limited resolution or patient movement, organ movements (e.g. bowel, uterus), or tissue deformation (e.g. tissue compression by the applicator, swelling, etc.) Further, when using x-ray or CT placement guidance, as suggested above, care must be taken to keep down the dose delivered through the imaging and CT time is often scarce. Also, x-ray imaging has limited soft tissue contrast, making it difficult to discern tumorous tissue, fat, or muscle.

Further, permanent placement of radioactive seeds (125-I or 103-Pd) in the prostate, known as low doserate (LDR) brachytherapy, is a widespread treatment method of early localized prostate cancer. The seeds are placed under ultrasound guidance using needles inserted through the perineum into the prostate. Specifically, the LDR procedure begins with insertion of a trans-rectal ultrasound (TRUS) probe for imaging the prostate base (distal side). For needle guidance, a hole array template is placed against the perineum. Two or three fixing catheters are peripherally placed to immobilize the prostate, and the resulting ultrasound image is used as spatial reference for catheter and seed positions in the prostate and any further images. Subsequently, the seed guiding catheters are inserted according to a pre-plan. For each catheter, the TRUS probe is positioned so that the catheter is visible. Any misplaced catheter is removed and inserted anew. The catheters deflect on insertion and their 3D position can hardly be assessed by 2D ultrasound. When seed placement is complete, a series of 2D ultrasound images are taken to characterize the final dose distribution. Additionally, CT or orthogonal fluoroscopic images are often taken a few weeks after implantation to determine the seed placements. The ultrasound guidance allows assessment of needle position but is unable to resolve the radioactive seeds throughout the whole prostate volume. This means that any misplacement of seeds relative to the preliminary plan is not known during the procedure and therefore cannot be compensated for by adaptive re-planning for the remaining seeds.

As such, a need exists for a localization and dose monitoring system, e.g. portal imaging for brachytherapy, that addresses these shortcomings. The present application describes a new and improved apparatus and method which overcomes these problems and others.

In accordance with one aspect, a system for interventional brachytherapy for generating data to be used directly for therapy and/or for therapy planning is provided. The system includes a radiation source which irradiates tissue of a patient and one or more radiation detectors which detect radiation delivered to the patient and generate radiation dosage data indicative thereof. One or more position sensors determine the position of the radiation source, and a localization unit, in communication with the one or more position sensors, generates position data indicative of the position of the radiation source. An image database stores one or more anatomical images of the patient. A dose calculation unit co-registers the one or more anatomical images with the positional and radiation dosage data and generates dose monitoring data based on the co-registration In accordance with another aspect, a method of brachytherapy therapy, directly for therapy and/or for therapy planning is provided. The method includes irradiating tissue of a patient with a radiation source, detecting radiation transmitting through the patient with one or more radiation detectors, generating radiation dosage data of the delivered radiation, determining the position of the radiation source with one or more position sensors, generating position data indicative of the position of the radiation source, retrieving one or more anatomical images of the patient, co-registering the one or more anatomical images with the positional and radiation dosage data, and generating dose monitoring data based on the co-registration.

In accordance with another aspect, a system for interventional brachytherapy for generating data to be used directly for therapy and/or for therapy planning is provided. The system includes a radiation source which irradiates tissue of a patient. One or more radiation detectors detect radiation delivered to the patient and generate radiation dosage data indicative thereof. One or more position sensors determine the position of the radiation source. An image database stores one or more anatomical images of the patient. One or more processor are programmed to communicate with the one or more position sensors, generate position data indicative of the position of the radiation source, co-register the one or more anatomical images with the positional and radiation dosage data, generate dose monitoring data based on the co-registration, and re-plan a radiation therapy plan based on the dose monitoring data.

One advantage resides in assured accuracy of a planned brachytherapy.

Another advantage resides in the real time tracking of radiation sources and detectors.

Another advantage resides in the real time monitoring of target volume and organ motion.

Still further advantages and benefits will become apparent to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

The present application is directed to a real time localization and dose monitoring system for portal imaging for brachytherapy. Specifically, a moving brachytherapy source and, in some embodiments, radiation detector(s) are tracked with a real-time, high-accuracy localization system. The localization system can be an optical shape sensing system (OSS) which tracks fiber sensors integrated into the source and the detector(s). Positioning information from other means, such as differential GPS (dGPS), impedance sensing, optical marker/camera measurements, or electromagnetic (EM) tracking are also contemplated. The information gathered by detection of the transmitted radiation and the localization system is combined with other imaging information originating e.g. from (TR)US, fluoroscopy, CT or optical, MM, fluorescence or infrared imaging, to provide multimodal images or dose monitoring data, including patient and organ motion/deformation for real time dose verification and adaptive re-planning of remaining fractions. Radiation dose simulators based on the same radiation-tissue interaction Monte-Carlo models are also contemplated for radiation therapy planning and account for the moving location of the tracked brachytherapy source relative to the target anatomy under treatment.

Figure 1:
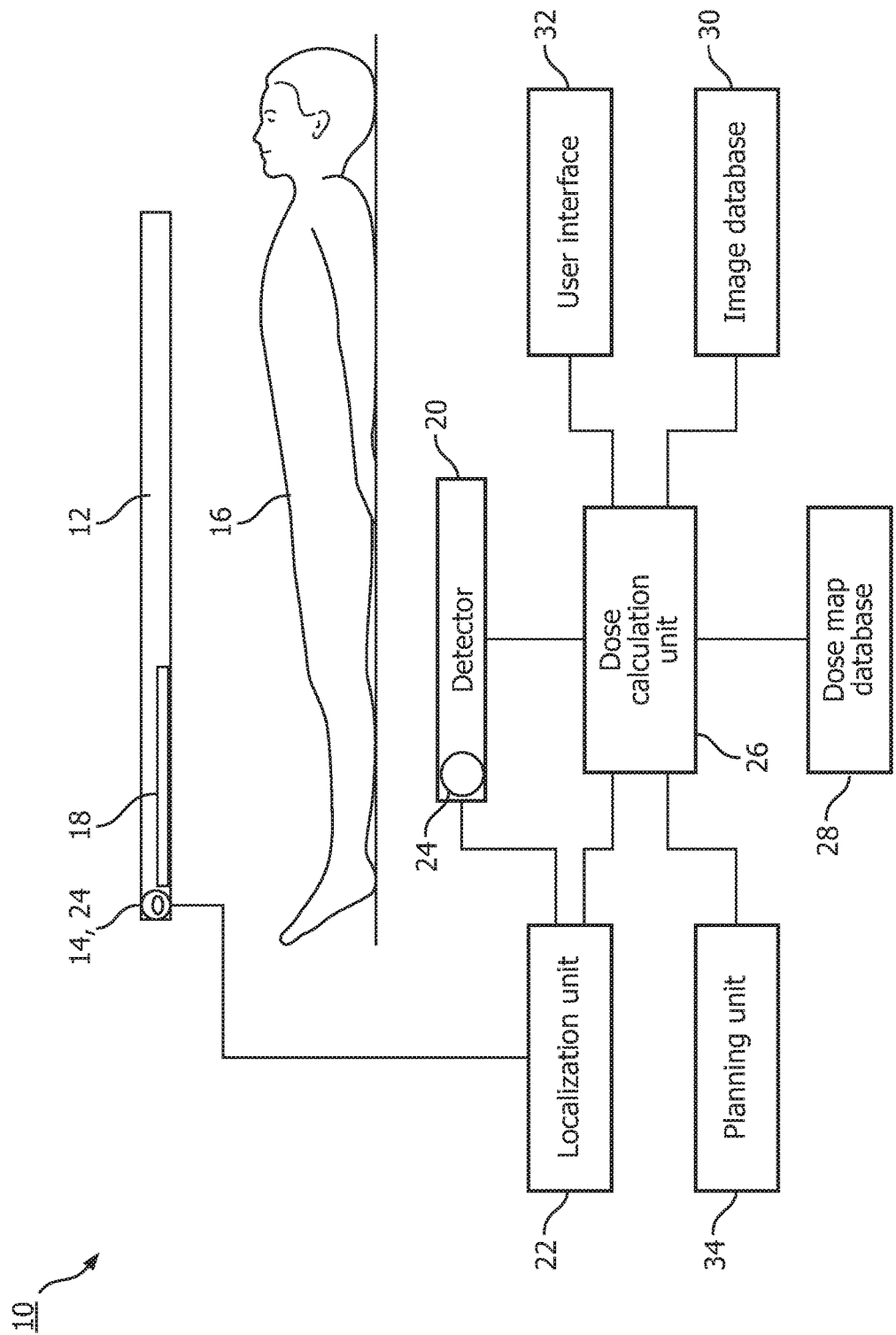
FIG. 1 is a diagrammatic illustration of a real time localization and dose monitoring system in accordance with the present application.

With reference to FIG. 1, a radiation therapy system 10 for real time localization and dose monitoring for portal imaging for brachytherapy is illustrated. The system 10 includes a radiation application apparatus 12 for inserting a radiation source 14 at a location within a patient or object 16. The radiation application apparatus 12 includes a catheter 18 for applying the radiation source 14 within the patient or object 16 at the desired location in accordance with a radiation therapy plan. Each therapy plan includes a plurality of fractions of radiation doses to be provided to desired location via the radiation source 14. Each radiation dose includes a prescribed radiation dose, a plurality of radiation beam trajectories, and at least one radiation source geometry. In another embodiment, the radiation application apparatus 12 includes a probe, endoscope, or other device used for image guided intervention. After the catheter 18 has been navigated to the desired location, the radiation source 14 is introduced to the patient or object 16. For example, a wire to a motor extends and retracts the radiation source 14 within the catheter 18 to prevent the patient or object 16 from unnecessary exposure to the radiation source 14. After the radiation source 14 has been moved to a desired location within the catheter 18, the radiation can be applied to, for example, a tumor within the person for destroying the tumor. In particular, the radiation source 14 can be inserted into a tumor cavity or in a natural lumen, in order to apply the radiation at and/or close to these locations.

In one embodiment, the radiation source 14 is an x-ray source for generating x-rays while an electrical energy is applied to the x-ray source. In this embodiment, the x-ray source is a miniature x-ray source operating at 20-70 kV that is arranged within the catheter. For example, the radiation source 14 is an x-ray tube type with a thermal filament as cathode and a transmission (for more or less isotropic x-ray emission) or so-called reflection (for directed emission) anode. An advantage with such so-called electron impact sources is that the energy of the radiation (the spectrum and maximum energy) can be tailored by selection of the anode material, the filtering, and the acceleration voltage employed. Another alternative would be a source with a pyroelectric or piezoelectric cathode, which would omit the need to supply high voltage to the tube electrodes in vivo. In another embodiment, the radiation source 14 is a high dose rate radioisotope (192-lr and the like) which is placed at the end of the catheter.

The radiation therapy system 10 further includes one or more external radiation detectors 20 which detect the radiation passing through tissue of the patient or object 16 between the radiation source 14 and the one or more radiation detectors 20 and generate radiation dosage information indicative thereof. In one embodiment, the one or more radiation detectors 20 are hand-held or mounted on a lightweight arm (potentially with automated arm actuation based on the position information of the source relative to the detector in order to ensure that measurements are obtained with optimal view angles/volume coverage). The one or more radiation detectors 20 may also include a substrate which is flexible or rigid, with localization measurements providing real-time feedback about detector geometry. Between the tissue of the patient or object 16 and the one or more radiation detectors 20, x-ray optics or collimating members may be incorporated. In procedures where a conventional C-arm or CT gantry is present, an x-ray detection sub-system utilizes the miniature x-ray source (mini-tube or radioactive isotope) for image acquisition.

A localization unit 22 tracks the positions and geometries of the radiation source 14 and/or the one or more radiation detectors 20 in real time and generates positioning information indicative thereof. To track the position of the radiation source 14, the radiation application apparatus 12 includes one or more position sensors 24 such as optical shape sensing (OSS) sensors. Likewise, the one or more radiation detectors 20 include OSS sensors within the detector elements. Optical shape sensing (OSS) utilizes light along a multicore optical fiber for device localization and navigation during a minimally invasive intervention. Shape sensing based on fiber optics exploits the inherent backscatter in a conventional optical fiber. The principle involved makes use of distributed strain measurement in the optical fiber using characteristic Rayleigh backscatter or controlled grating patterns. The shape of the optical fiber is defined from a specific point along the sensor, known as the launch or z=0, and the subsequent shape position and orientation are relative to that point. An optical shape sensing sensor tethered to the radiation application apparatus 12 includes bare optical fiber that is connected at one end, terminated at the tip to suppress reflections, and contains a launch point along the tether that serves at the origin of the shape reconstruction. Each tether is calibrated for shape sensing using a straight reference and wobble reference in a spiral path plate. Following calibration the bare fiber is then integrated into a device via any number of methods (attachment, embedding, adhesion, electro/magnetic attraction or other coupling means) during a manufacturing process. This integration process can affect the robustness and accuracy of the optical shape sensing. In addition, following integration a registration must be performed to determine the non-linear spatiotemporal transformation which maps the dynamic geometry of the flexible instrument to the shape sensing measurements at any instant. This includes the registration of the shape sensing coordinate system to the launch fixture/instrument coordinate system. In another embodiment, the position sensors 24 include differential GPS (dGPS), impedance sensing, optical marker/camera measurements, or electromagnetic (EM) guidance, and the like.

A dose calculation unit 26 generates one or more dose maps for real time dose monitoring from the radiation dosage information detected by the one or more radiation detectors 20 and the positioning information determined by the localization unit 22. In another embodiment, the one or more radiation detectors 20 are configured to be rotatable around the patient or object 16 such that the dose calculation unit 22 generates a 3D dose map. The dose calculation unit 26 then stores the one or more dose maps in a dose map database 28. To accomplish the real time dose monitoring, the radiation therapy system 10 further includes a diagnostic imaging system that generates anatomical images of the patient. In one embodiment, the anatomical images are used as input information to the radiation therapy system 10 to determine the location of a target of a patient. In another embodiment, the anatomical images are combined with the dose maps to provide multi-modal images or dose monitoring data. The diagnostic system may be a Computed Tomography (CT) scanner, a Magnetic Resonance Imaging (MM) scanner, a Positron Emission Tomography (PET) scanner, an ultrasound device, an x-ray device, a fluorescence or infrared scanner, and the like. Preferably, the anatomical images are 3D images of the anatomy of the patient and are stored in an image database 30. Prior to administration of a radiation dose, the diagnostic imaging system acquires anatomical image data representing of a target volume and non-target volumes of the patient. The anatomical image data including pre-registered anatomical images, real-time ultrasound images during catheter placement, and the like. In one embodiment, a motion model predicts the target and non-target volumes' positions during treatment including patient and organ motion/deformation. The anatomical image data is then digitized and processed to reconstruct the anatomical images using one of many well-known reconstruction techniques. It should be contemplated that the reconstruction of anatomical images based on extended or point-like internal sources that move over time need to be augmented to account for the time-varying nature of the radiation source/detector geometry relative to the patient anatomy. For these reconstructions, rapid iterative reconstruction is utilized since dynamic models of the imaging geometry relative to the patient anatomy can be coupled with real-time positional information derived from the localization unit 22.

The dose calculation unit 26 combines the one or more dose maps and the anatomical images to provide multi-modal images or dose monitoring data, including patient and organ motion/deformation for real time dose verification and adaptive re-planning of remaining fractions. In one embodiment, the dose calculation unit 26 co-registers the localized dose map from the tracked radiation source 14 and/or one or more radiation detectors 20 with the anatomical images to generate a visualization of a localized dose map of the delivered dose to the various portions of the anatomy. Specifically, after the radiation dose is delivered, the dose calculation unit 22 determines the actual dose delivered to each voxel of a target based on the anatomical image and the one or more dose maps. Based on this determination, the dose calculation unit 22 generates multi-modal images or dose monitoring data indicative for real time dose monitoring and verification including a localized dose map. In one embodiment, dose monitoring data is utilized to verify the radiation dose distribution against the radiation therapy plan. In another embodiment, the multi-mode images are utilized to monitor the radiation dose being delivered in real time. The multi-modal images and/or dose monitoring data are displayed on a display of a user interface 32. The user interface 32 also includes a user input device which a clinician can use for controlling the view of the multi-modal images and/or dose monitoring data, updating the radiation therapy plan, and the like.

In one embodiment, a planning processor 34 updates the radiation therapy plan, i.e. at least one or all of the subsequent radiation doses, automatically based on the dose monitoring data. In another embodiment, radiation plan is updated under user guidance, e.g. by a physician or clinician. The physician verifies the delivered radiation dose in real time on the user interface 32. Using the input device and the multi-modal images, the physician can identify the target volume and non-target volumes, i.e. sensitive tissue, organs, or the like. The planning processor 60 updates the remaining radiation therapy plan, i.e. at least one or all of the radiation doses, according to the actual radiation delivered to the target volume and non-target volumes.

In another embodiment, radiation dose simulators based on the same radiation-tissue interaction Monte-Carlo models are also contemplated for updating the radiation therapy plan and account for the moving location of the tracked radiation source relative to the target anatomy under treatment. Adaptive radiation treatment planning based on Monte-Carlo methods and radiation-tissue interaction models do not currently exploit additional information about the location of moving source/detector components within the target tissue. The ability to leverage dynamic measurements of location in such dose mapping models would allow for greater adaptation/optimization of brachytherapy plans, accounting in real-time for any changes occurring to the tissue and to the devices within the anatomy.

In another embodiment, the radiation therapy system 10 includes an ultrasound device separate or integrated into the radiation application apparatus 12. For low dose rate (LDR) prostate cancer treatment, radioactive seeds are permanently placed under ultrasound guidance using needles inserted through the perineum into the prostate. The ultrasound guidance (a rectally placed US-probe and the like) allows approximate assessment of needle position but is unable to resolve the radioactive seeds throughout the whole prostate volume. This prevents efficient real-time re-planning which would be relevant for every seed that is misplaced according to the initial dose plan. The multi-modal imaging using a combined x-ray source and ultrasound device would circumvent this problem and allow for low-dose real-time re-planning. Such a system would also allow for higher resolution than the use of ultrasound alone. Using a miniature x-ray source, the energy, the dose rate, and the directionality of the radiation source could be adjusted inter- and/or intrafractionally based on real-time dose monitoring data.

Figure 2:
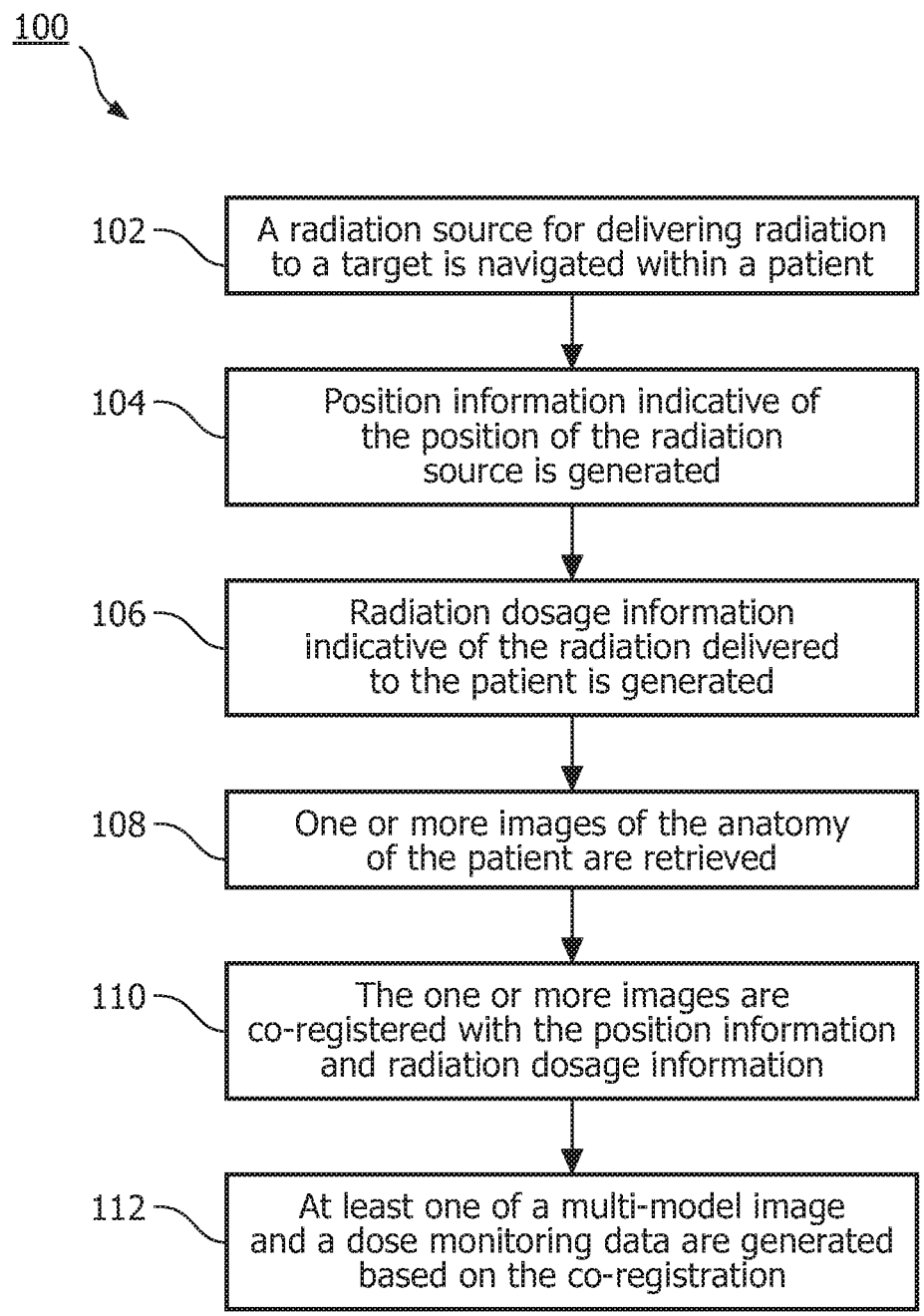
FIG. 2 is a flow chart of a method for real time localization and dose monitoring in accordance with the present application.

FIG. 2 illustrates a method 100 for real time localization and dose monitoring. In a step 102, a radiation source for delivering radiation to a target is navigated within a patient. In a step 104, position information indicative of the position of the radiation source is generated. In a step 106, radiation dosage information indicative of the radiation delivered to the patient (e.g. the local dosimetry) is generated. In a step 108, one or more images of the anatomy of the patient are retrieved. In a step 110, the one or more images are co-registered with the position information and radiation dosage information. In a step 112, at least one of a multi-modal image and a dose monitoring data are generated based on the co-registration.

The above provides a portal imaging method for in situ brachytherapy monitoring. Because of the non-fixed source, combination with high-resolution means of source and detector position determination is necessary. The localization system can be e.g. an optical shape sensing system (OSS) which tracks both the source and the detector in real-time, or only the source if the detector is fixed and stiff. The information gathered by detection of the transmitted radiation can be combined with other imaging information to provide multi-modal images or dose monitoring data, including patient and organ motion or deformation for dose verification and adaptive re-planning of remaining fractions. This allows for real-time adaptive re-planning during this time-consuming procedure. Other potential uses include endoscopic procedures in ducts and lumens of human subjects or animals, for diagnosis, treatment guidance, monitoring, and follow-up. The clinical applications include gynaecological diseases, rectal, urinary and prostate diseases, as well as esophaegal and bronchial applications, laparoscopy, minimally invasive procedures like ablation and IGIT. The inserted x-ray source may be combined with US (as in the prostate LDR case), or e.g. with optical imaging as for gastroscopy. Another potential application is the treatment of prostate cancer which has earlier been treated by LDR brachytherapy. In this case, already implanted Pd or I seeds are present throughout the prostate.

One having ordinary skill in the art will appreciate in view of the teachings provided herein, features, elements, components, etc. described in the present disclosure/specification and/or depicted in the appended Figures and/or any other Appendixes, may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read-only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for systems, methods and others, for example (which embodiments are intended to be illustrative and not limiting), it is noted that modifications and variations can be made by persons skilled in the art in light of the teachings provided herein, including the Figures and Appendixes. It is therefore to be understood that changes can be made in/to the preferred and exemplary embodiments of the present application which are within the scope of the embodiments described herein. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system for interventional brachytherapy for generating data to be used directly for therapy and/or for therapy planning, said system comprising:
   a radiation source configured to be inserted into a patient to irradiate tissue of the patient;
   one or more radiation detectors configured to be disposed outside the patient to detect radiation from the radiation source after the radiation has been transmitted through the patient and generate radiation dosage data in real time indicative thereof, the one or more radiation detectors being displaced from the patient and freely movable relative to the radiation source and the patient;
   a plurality of position sensors including a first position sensor configured to determine a position of the radiation source in real-time and a second position sensor configured to determine a position of the one or more radiation detectors in real-time;
   a localization unit, in communication with the plurality of position sensors, which generates position data indicative of the position of the radiation source;
   an image database which stores one or more anatomical images of the patient; and
   a dose calculation unit which co-registers the one or more anatomical images with the positional and radiation dosage data and generates dose monitoring data based on the co-registration.

2. The system according to claim 1, wherein the plurality of position sensors include optical shape sensing (OSS) sensors which track fiber sensors integrated into the radiation source.

3. The system according to claim 1, wherein the position sensors include at least one of differential Global Positioning System (dGPS), impedance sensing, optical marker/camera measurements, and electromagnetic (EM) tracking.

4. The system according to claim 1, wherein the radiation source includes a miniature x-ray source.

5. The system according to claim 1, wherein the dose calculation unit determines a radiation dose actually delivered to each voxel of the tissue based on the co-registered one or more anatomical images and the radiation data.

6. The system according to claim 5, further including:
   a real-time ultrasound imaging system configured to generate images depicting organ motion and deformation, the dose calculation unit determining the radiation dose actually delivered to each voxel of the tissue based further on the ultrasound images.

7. The system according to claim 1, wherein the dose calculation unit further generates multi-modal images in real time from the dose monitoring data and anatomical images, the multi-modal images depicting radiation dose delivered to each voxel of the tissue.

8. The system according to claim 1, wherein a planning unit re-plans a radiation treatment plan based on the dose monitoring data.

9. The system according to claim 1, wherein the radiation source is 192-Ir.

10. The system according to claim 1, wherein at least one of the one or more radiation detectors are hand held to be freely positionable relative to the source.

11. A system for interventional brachytherapy for generating data to be used for therapy or therapy planning, the system comprising:
   a computer database configured to store an anatomical image of a patient suitable for identifying target and non-target tissues;
   a real-time imaging system configured to generate images of the patient in real-time;
   a radiation source configured to be inserted into the patient to a location near the target tissue to irradiate the target tissue, the radiation source being coupled with a first position sensor configured to indicate a position of the radiation source;
   one or more radiation detectors configured to receive radiation from the radiation source after the radiation has passed through the patient and to generate radiation dosage data in real-time indicative of the received radiation, the one or more radiation detectors including additional position sensors, the additional position sensors being configured to indicate a location of each of the one or more radiation detectors, the one or more radiation detectors and the additional position sensors being configured to be displaced from the patient and move relative to the patient, the target tissue and the radiation source;
   a workstation including a display and a user input device; and
   one or more computer processors configured to:
      retrieve the anatomical image from the computer database and control the workstation display to display the anatomical image,
      detect the locations of the first and additional position sensors and the radiation dose detected by the one or more radiation detectors,
      generate a dose map indicative of a cumulative dose delivered to the target tissue based on the determined first and additional position sensor locations, the detected radiation dose, the real-time image, and a motion model that predicts target tissue and non-target tissue volume locations during treatment attributable to organ motion and/or deformation,
      control the workstation display to display a representation of the cumulative dose superimposed on the anatomical image.

12. The system according to claim 11, wherein the one or more computer processors are further configured to:
   retrieve the anatomical image from the computer database,
   develop a brachytherapy plan based on inputs from the user input device, and
   verify and adaptively re-plan the brachytherapy plan based on the cumulative dose.

13. The system according to claim 12, wherein the brachytherapy plan includes a plurality of fractions of radiation doses to be provided to a desired location via the radiation source and the one or more computer processors are further programmed to: adaptively re-plan the fractions of radiation doses during therapy.

14. The system according to claim 12, wherein the re-planning the brachytherapy plan is performed in real-time based on the cumulative dose and organ motion and/or deformation.

15. The system according to claim 11, wherein at least one of the one or more radiation detectors are hand held to be freely movable and positionable relative to the radiation source and the patient.

* * * * *